United States Patent [19]

Amer

[11] Patent Number: 4,591,718

[45] Date of Patent: May 27, 1986

[54] PHOTOTHERMAL METHOD FOR IN SITU MICROANALYSIS OF THE CHEMICAL COMPOSITION OF COAL SAMPLES

[75] Inventor: Nabil M. Amer, Berkeley, Calif.

[73] Assignee: The United States of America as represented by the United States Department of Energy, Washington, D.C.

[21] Appl. No.: 545,338

[22] Filed: Oct. 25, 1983

[51] Int. Cl.$^4$ .................... G01J 5/08; G01N 21/63
[52] U.S. Cl. ................... 250/339; 356/432; 374/45
[58] Field of Search ............ 374/32, 17, 45, 130, 374/5; 356/128, 432; 250/318, 343, 339

[56] References Cited

U.S. PATENT DOCUMENTS

| | | | |
|---|---|---|---|
| 4,030,837 | 6/1977 | Kojima et al. | 356/30 X |
| 4,048,499 | 9/1977 | Kreuzer | 250/344 |
| 4,061,918 | 12/1977 | Preier et al. | 250/343 |
| 4,310,762 | 8/1984 | Harris et al. | 250/343 |
| 4,468,136 | 8/1984 | Murphy et al. | 374/45 |
| 4,540,285 | 9/1985 | Amer | 356/42 |

OTHER PUBLICATIONS

Photothermal Deflection Spectroscopy and Detection, W. B. Jackson et al., Applied Optics, 4/15/81, vol. 20, No. 8, pp. 1333-1344.
"A Sensitive Photothermal Deflection Technique for Measuring Absorption in Optically Thin Media", by A. C. Boccara et al.; Apr. 1980, Lawrence Berkeley Lab., (LBL-10793 Reprint), (Calif.), pp. 1-11.
"Sensitive In Situ Trace Gas Detection by Photothermal Deflection Spectroscopy", by D. Fournier et al., Mar. 1980, Lawrence Berkeley Lab., (LBL-10695 Reprint), (Calif.), 374-5.

*Primary Examiner*—Daniel M. Yasich
*Attorney, Agent, or Firm*—L. E. Carnahan; Roger S. Gaither; Judson R. Hightower

[57] ABSTRACT

Successive minute regions (13) along a scan path on a coal sample (11) are individually analyzed, at a series of different depths if desired, to determine chemical composition including the locations, sizes and distributions of different maceral inclusions (12). A sequence of infrared light pulses (17) of progressively changing wavelengths is directed into each minute region (13) and a probe light beam (22) is directed along the sample surface (21) adjacent the region (13). Infrared wavelengths at which strong absorption occurs in the region (13) are identified by detecting the resulting deflections ($\phi$) of the probe beam (22) caused by thermally induced index of refraction changes in the air or other medium (19) adjacent the region (13). The detected peak absorption wavelengths are correlated with known characteristic peak absorption wavelengths of specific coal constituents to identify the composition of each such minute region (13) of the sample (11). The method enables rapid, convenient and non-destructive analyses of coal specimens to facilitate mining, processing and utilization of coals.

10 Claims, 2 Drawing Figures

PHOTOTHERMAL METHOD FOR IN SITU MICROANALYSIS OF THE CHEMICAL COMPOSITION OF COAL SAMPLES

BACKGROUND OF THE INVENTION

This invention relates to methods for analyzing the chemical composition of coal. More particularly, the invention relates to a non-destructive method employing photothermal spectroscopic techniques to detect coal constituents including, in a preferred form of the invention, the detection of variations of chemical composition at successive microscopic regions of a coal sample. The United States government has rights in this invention pursuant to contract number DE-AC-03-76SF00098 between the U.S. Department of Energy and the University of California.

The morphological structure of coal typically exhibits a mixture of chemically distinct inclusions or macerals such as vitrinite, exinite, micronite and fusinite among others. Such macerals may be present in varying proportions and in varying sizes in coals obtained from different mines or different sites within a particular mine.

Different types of maceral have different chemical compositions and significantly different chemical behaviors. Consquently, analysis of the maceral composition of particular coal samples can be very useful in connection with selecting particular coals for particular usages. For example, the maceral composition is a major determinant of the rank or heat producing capability of a coal. As a further example, the macerals vitrinite and exinite are readily susceptible to liquifaction while micrinite and fusinite are not. Significant physical properties, such as hardness for example, are also determined in part by the types, sizes and distribution of the various macerals within the coal.

As macerals are typically microscopic inclusions in coal, identifying the chemical compositions and preferably the sizes and distributions of particular macerals requires techniques capable of resolving the desired information at the microscopic level. This cannot be accomplished by conventional methods of chemical analysis unless an undesirably complex and lengthy series of exacting operations are performed. In particular, the coal sample must be physically separated into minute portions each of which must then be separately analyzed and the resulting data must then be correlated with the original locations of the minute portions in the sample.

Thus the processing and utilization of coal can be greatly facilitated by a more convenient and preferably non-destructive method for analyzing the chemical composition of coal on a microscopic scale. Preferably, the method should detect variations of chemical composition between very minute successive regions including regions at different depths to enable evaluation of the maceral composition of a three dimensional portion of a coal sample.

SUMMARY OF THE INVENTION

It is an object of this invention to provide an accurate and convenient method for analyzing the chemical composition of minute regions of coal samples.

It is a further object of the invention to provide a more efficient procedure for detecting variations of chemical compositions at successive minute regions along the surface of a coal sample.

It is another object of the invention to provide a non-destructive method for analyzing the chemical composition of minute regions of a coal sample which are situated at different depths within the sample.

It is still another object of this invention to facilitate evaluation of the maceral composition of coals including identification of the types, sizes and distributions of different component macerals within a three dimensional portion of a coal sample.

Additional objects, advantages and novel features of the invention will be set forth in part in the description which follows, and in part will become apparent to those skilled in the art upon examination of the following or may be learned by practice of the invention.

The objects and advantages of the invention may be realized and attained by means of the instrumentalities and combinations particularly pointed out in the appended claims.

To achieve the foregoing and other objects and in accordance with the purposes of the present invention, as embodied and broadly described herein, identifying chemical constitutents of a localized region of a coal sample includes the steps of directing at least one sequence of infrared light pulses into the sample region, varying the wavelength composition of successive ones of the infrared light pulses of the sequence, detecting thermally induced index of refraction changes in the medium adjacent the sample region that accompany optical absorption of the infrared light pulses in the sample region, correlating the index of refraction changes with the particular infrared light pulse wavelengths that initiate the changes, and identifying the chemical constituents of the sample region by correlating the particular wavelengths with the characteristic peak infrared absorption wavelengths of specific coal constituents.

Preferably, in another aspect of the invention, the index of refraction changes are detected by directing a probe beam of light along the surface of the coal sample and through the portion of the medium that is adjacent the sample region, and by detecting the amount of deflection of the probe beam that is caused by each of the infrared light pulses of the sequence.

Preferably, in another aspect of the invention, the sequence of infrared light pulses is generated by directing a continuous beam of infrared light towards the sample, progressively shifting the wavelength composition of the continuous beam through at least a predetermined portion of the infrared spectrum, and cyclically interrupting the continuous beam to convert the continuous beam into discrete spaced apart pulses which have equal durations.

Preferably, in another aspect of the invention, the steps are repeated at the same region of the sample utilizing an additional sequence of infrared light pulses which are of different duration than the pulses of the first sequence whereby constituents of the sample at a different depth may be identified.

Preferably in still another aspect of the invention, the steps are repeated at each of a series of successive regions situated along a scan path on the sample whereby variations of the chemical composition of the sample along the scan path may be identified.

The invention provides for analysis of the chemical composition of minute regions of coal samples in a rapid, accurate and efficient manner and without requiring physical or chemical breakdown of the samples. In a preferred form of the invention, a separate chemical analysis may be made at each of a series of successive small regions along a scan path on the sample and at each such region variations of chemical composition at a series of different depth may be detected. The resulting data enables identification of the types, sizes and locations of component macerals within the scanned region of the coal sample. Suitability of the particular coal for different specific uses may then be more precisely evaluated.

BRIEF DESCRIPTION OF THE DRAWINGS

The accompanying drawings which are incorporated in and form a part of the specification, illustrate a preferred embodiment of the invention and, together with the description, serve to explain the principles of the invention. In the drawings.

DETAILED DESCRIPTION OF THE INVENTION

Reference will now be made to the present preferred embodiment of the invention, which is illustrated in the accompanying drawings.

Figure 1:
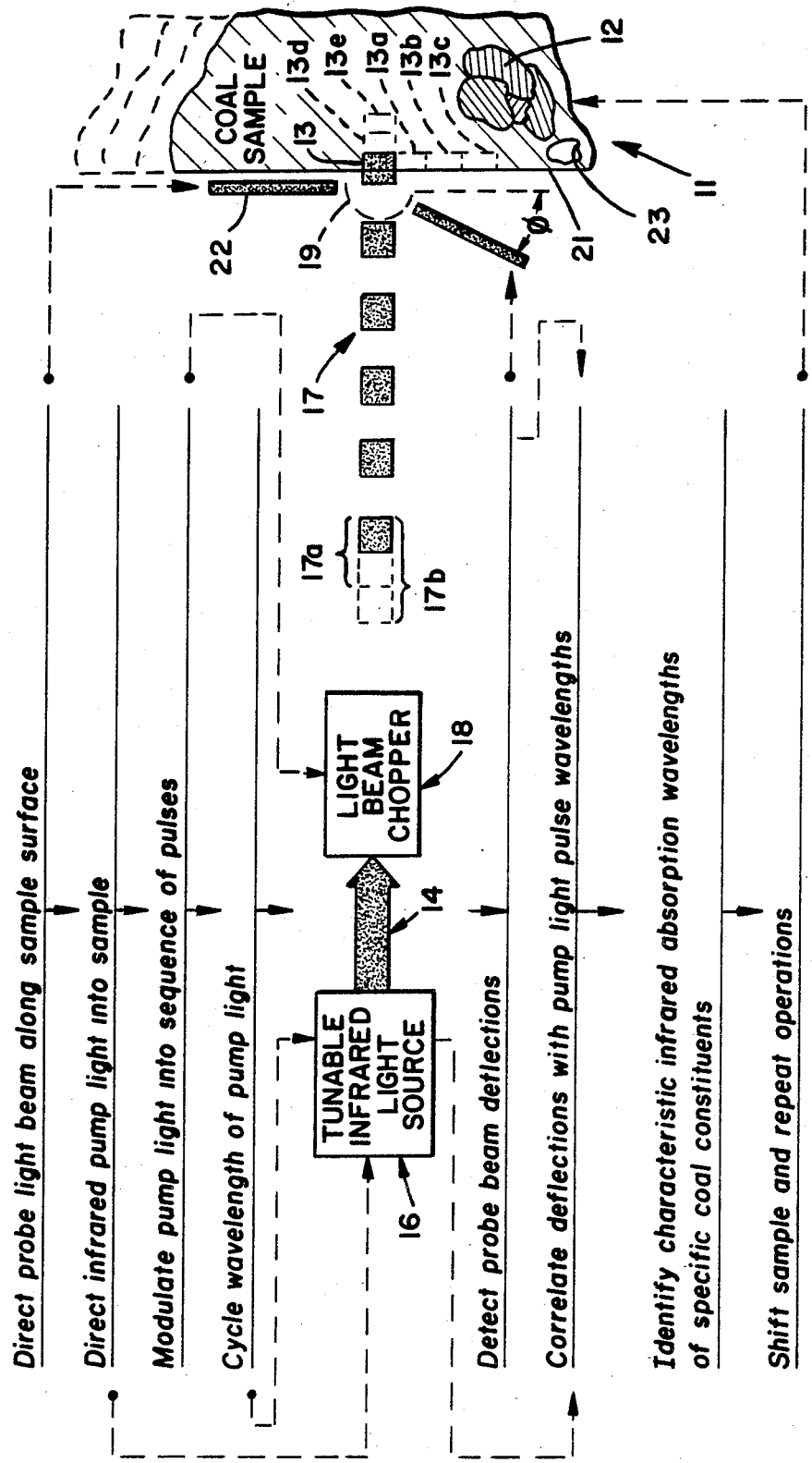
FIG. 1 is a diagramatic illustration of operations performed on a coal sample, in accordance with one embodiment of the invention, in order to analyze chemical composition including variations of chemical composition and maceral morphological structure within a predetermined surface layer of the sample.

Referring to FIG. 1 of the drawings, a coal sample 11 is primarily composed of a mixture of macerals 12 or inclusions individual ones of which may be of any of a limited number of chemically distinct types. Differences in the chemical and physical behavior of coals are primarily attributable to differences in the types of maceral 12 which are present, the relative abundances of the different types and the sizes and distributions of different macerals in the particular coals. Thus a convenient procedure for evaluating these properties can greatly facilitate the mining, processing and utilization of coals.

The present method makes use of the fact that different types of maceral 12 exhibit distinctive differences of optical absorption coefficient for specific wavelengths or frequencies of infrared light. This is not the case with respect to wavelengths in the visible light portion of the spectrum as evidenced by the blackness or lack of coloration of coal when illuminated with polychromatic visible light. All visible wavelengths are uniformly, substantially completely absorbed. Infrared absorption differs in that it is dependent on wavelength and on the chemical composition of the coal thereby providing a mechanism by which the constitutents of the coal may be identified.

In particular, if infrared light is directed to a small surface region of coal that is of uniform chemical composition as occurs if the region is occupied by a single maceral type and the wavelength composition of the infrared light is progressively varied through the full infrared spectrum then relatively stong absorption peaks occur at one or more specific wavelengths and lesser secondary absorption peaks occur at one or more other wavelengths in most cases. These characteristic peak infrared absorption wavelengths are different for each different type of maceral 12 owing to differences in the chemical compositions of the maceral types. Optical absorption of infrared energy is fundamentally an interaction between individual photons and individual molecules and molecules of a particular chemical compound interact significantly only with photons of one or more specific wavelengths.

Thus the chemical composition and therefore the maceral composition of a minute region 13 of a coal sample can be identified by detecting the particular infrared wavelenths at which absorption peaks occur and then correlating such wavelengths with the characteristic peak absorption wavelengths of specific chemical compounds or maceral types.

To accomplish this in accordance with this embodiment of the invention, a continuous beam 14 of infrared light is directed toward the sample region 13 utilizing an infrared source 16 of the form which emits a single wavelength or narrow band of wavelengths at any instant but which is tunable to enable a progressive variation of the wavelength composition of the beam 14. Between the source 14 and coal sample 11 beam 14 is modulated into a first sequence of infrared light pulses 17 which have equal durations. A suitable example of a modulator or beam chopper 18 for this purpose as well as other apparatus components for performing the desired operations will be hereinafter described in more detail.

Infrared light energy which is absorbed in the sample region 13 converts to heat energy. Such heat then diffuses away from region 13 in all directions including into the air or other gaseous or liquid medium 19 adjacent the surface 21 of the coal sample 11. This creates a temporary thermal gradient in the adjacent medium and also a temporary index of refraction gradient as the index of refraction of gases or liquids is a function of temperature. The magnitude of the temporary index of refraction gradient which accompanies each infrared pulse 17 is a function of the amount of heat generated in sample region 13 by the pulse.

The energy content of the successive infrared pulses 17 is substantially constant as the pulses originate from the same source 16 and have equal durations. Consequently, the magnitude of the index of refraction gradient which accompanies each pulse 17 depends on the efficiency of the absorption process in sample region 13. Infrared energy which is not absorbed in region 13 either penetrates more deeply before being converted to heat and therefore has a reduced effect on the index of refraction or is radiated from the sample 11 in nonthermal forms by processes such as reflection or fluorescence.

Thus the degree of absorption of each pulse 17 within sample region 13 can be ascertained by detecting the magnitudes of the accompanying index of refraction changes in the adjacent medium 19. A preferred procedure for this purpose includes directing a probe light beam 22 along the surface 21 of the sample 11 with the probe light beam being oriented to intersect the infrared pulse 17 path at the portion of the medium 19 which is adjacent sample region 13. The probe light beam 22 is preferably situated as close to the sample 11 as is realizable without disruption of the beam by irregularities in the sample surface and preferably has a diameter, in the vicinity of sample region 13, that is smaller than the diameter of the infrared light pulses 17.

Index of refraction gradients produced by successive ones of the infrared light pulses 17 of progressively changing wavelength composition are individually detected by sensing the resulting momentary deflections, $\phi$, of probe light beam 22 that result from the gradients. The magnitude of each such deflection $\phi$ is a function of the optical absorption coefficient of the substance at sample region 13 for the particular wavelength or narrow band of wavelengths in the infrared light pulse that causes the deflection.

Graphically and/or by data processing equipment, relatively large or peak deflections $\phi$ are correlated with the infrared wavelengths that are being emitted by source 16 at corresponding times during the sequence of infrared pulses 17.

The composition of sample region 13 may then be readily ascertained by comparing the detected peak absorption wavelengths with the characteristic peak absorption wavelengths of different specific coal constituents. Chemically pure elements or compounds always exhibit the same absorption spectra which are available in the literature in many cases or which are readily obtained by trial runs on pure samples. This is not true of coal macerals 12 which may vary in chemical composition at different geographical locations. Consequently, the characteristic peak absorption wavelengths of vitrinite or exinite, for example, mined in the State of Utah may differ from those of the same macerals 12 in coal mined in Pennsylvania. Thus the initial practice of the method at a particular location should be preceded by a calibration in which the peak absorption wavelengths of the different macerals 12 from that location are ascertained by performing the method on pure samples of each maceral from that location.

The infrared light pulses 17 may be focussed down to diameters as small as several microns at the point of penetration into coal sample 11. Thus the sample region 13 may be correspondingly small and may often be entirely within a single maceral 12. Detection of combinations of characteristic peak absorption wavelengths indicates that the same region 13 straddles one or more boundaries between macerals 12 of different type. Variations of chemical composition between successive minute portions of the coal sample 11, including identifications of the locations sizes and distributions of individual macerals 12 may thus be detected by repetitively shifting sample 11 relative to infrared source 16 in order to repeat the above described steps at each of a series of adjacent sample regions 13a, 13b, 13c and the like within a scan raster pattern.

Such identification of the chemical composition of each of a series of successive minute regions 13, 13a, 13b, 13c enables evaluation of the proportion of different maceral 12 types that are present in the particular coal sample 11 and may also be used to prepare a constructed image or mapping of the macerals in the sample.

The microanalysis of the chemical composition of the sample 11 may be done on a three dimensional basis if more detailed information is needed. For this purpose the composition of a series of additional sample regions 13d, 13e, situated at progressively greater depths within the sample 11, is determined in conjunction with analysis of each of the series of surface regions 13, 13a, 13b, 13c. Following the hereinbefore described analysis of the composition of a surface region 13, the tunable infrared light source 16 is operated to direct a second sequence of infrared light pulses 17a of progressively varied wavelengths into the sample 11 at the same point but with the modulator or beam chopper 18 slowed so that the pulses 17a of the second sequence have a longer duration than the pulses 17 of the first sequence. Preferably, the rate at which the output wavelength of source 16 is varied is also slowed proportionately so that the sequence of longer infrared pulses 17a includes the same number of pulses as the previous sequence.

As the infrared light pulses 17a of the second sequence are of longer duration, the energy content of each pulse is greater than in the previous case and penetrates more deeply into the sample 11 as depicted diagramatically at 13d. An evaluation of chemical composition made in conjunction with the second sequence of infrared light pulses 17a, in accordance with the previously described steps, is thus indicative of the composition of a deeper portion of the sample that includes both the surface region 13 and the subjacent region 13d.

The composition of the subject region 13d in particular may then be determined by subtracting absorption peak values previously detected at particular wavelengths during the analysis of surface region 13 from any absorption peak values detected at the same wavelengths during the second sequence of infrared pulses 17a. The adjusted absorption peaks may then be identified as characteristic absorption peaks of specific coal constituents in the manner previously described to ascertain the composition of region 13d as such.

Analysis of the sample 11 at still deeper regions 13e may then be accomplished by repeating the above described operations with sequences of infrared pulses 17b of still greater durations. The maximum penetration depth of infrared pulses 17 of practical intensities is limited by the high opacity of coal but as the successive regions 13, 13d, 13e typically have depths of only several microns, the process still enables three dimensional analysis to an extent that provides significantly more detailed information than is obtained if only the surface regions 13, 13a, 13b, 13c are analyzed.

The magnitudes of the deflections $\phi$ of probe beam 22 and thus the peak absorption values are detected are reduced if one or more porosities 23 are present in a sample region 13 that is being analyzed. The infrared pulses 17 then penetrate more deeply and consequently less heat is transferred to the adjacent medium 19. This does not prevent identification of characteristic peak absorption wavelengths as all such peaks that may be detected are uniformly reduced and the relative sizes of such peaks remain apparent. The uniform reduction in the sizes of absorption peaks as detected enables detection and locating of the porosities 23 as such if it is desired to include porosities in the compositional analysis of the sample 11.

The probe beam deflection $\phi$ which typically occurs has been exaggerated in FIG. 1 for clarity of illustration. Similarly, there are usually more infrared pulses 17 in a sequence and more regions 13 are individually analyzed than can be clearly depicted in the drawing. In a typical analysis of a coal sample 11, the beam chopper 18 may be operated initially to provide infrared light pulses 17 at a frequency of about 1 kHz while the median output wavelength of the infrared source 16 is progressively varied from about 3 microns to about 15 microns. During subsequent sequences of the infrared light pulses 17, to obtain readings at progressively greater depths in the sample 11 as previously described, the infrared light pulse 17 frequency may be reduced in steps to about 1 Hz, for example. The infrared light pulses 17 are typically focussed down to a diameter of about 10 microns at the surface 21 of the sample 11 and the probe beam 22 may have a diameter of about 5 microns at the region of intersection with the infra red light pulses 17.

It should be understood that these specific values for various parameters have been set forth for purposes of example only and should not be considered to be limitative of the practice of the invention as other values for any of the above specified parameters may also be suitable.

Figure 2:
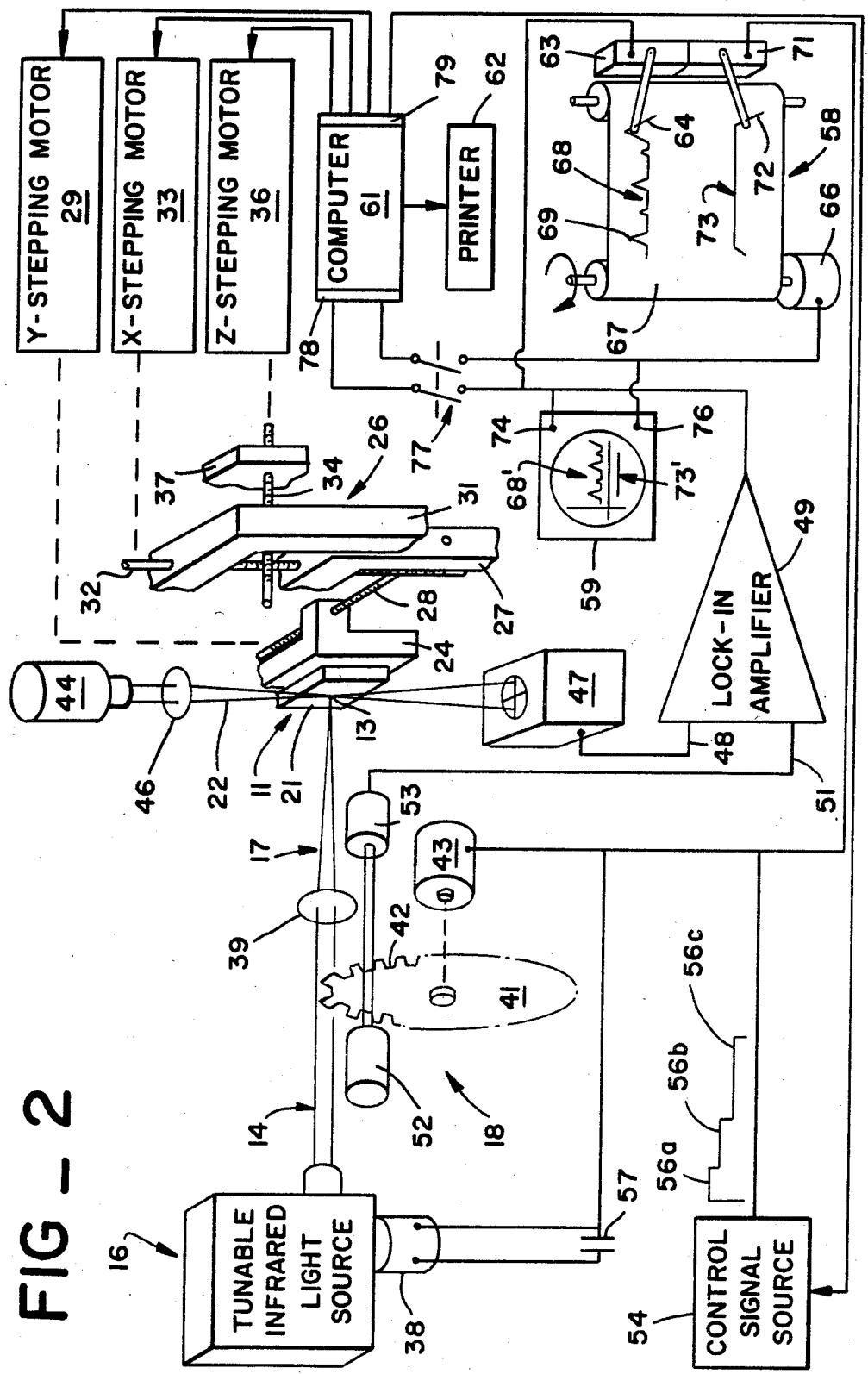
FIG. 2 is a schematic depiction of apparatus which may be used to perform an analysis of the composition of a coal sample in accordance with the method of FIG. 1.

FIG. 2 of the drawing depicts one example of apparatus suitable for performing the hereinbefore described steps, other types of apparatus or arrangements of components also being adaptable to the purpose.

In the system of FIG. 2, the coal sample 11 which is to be analyzed is temporarily mounted on a specimen holder platform 24 that is controllably translatable in each of three mutually perpendicular directions. The translation means 26 may, for example, be similar to that employed in motor controlled microscope states. Thus specimen holder 24 is slidable in a first or Y-axis direction, relative to a first stage frame 27, in response to rotation of a first lead screw 28 driven by a Y-axis stepping motor 29. First frame 27 is in turn slidable in a perpendicular or X-axis direction, relative to a second stage frame 31, in response to rotation of a second lead screw 32 driven by an X-axis stepping motor 33. The second frame 31 is movable in the third or Z-axis direction by rotation of a third lead screw 34, driven by Z-axis stepping motor 36, that is coupled to a stationary member 37 of the translation means 26.

The infrared light source 16 in the system of FIG. 2 is a tunable source, such as a Xennon arc lamp with variable bandpass filter, of the known type in which the wavelength composition of the infrared output beam 14 may be progressively varied in a cyclical manner by operation of a grating drive motor 38. Such sources 16 transmit only a narrow range of wavelengths at any one instant but are adjustable to sweep the transmited range of wavelength progressively through at least a portion of the infrared spectrum. Tunable infrared lasers may also be utilized as the infrared light source 16 although more than one laser may be needed to provide the full range of wavelengths used in the practice of the method.

Infrared light 14 from source 16 is directed to the coal sample 11 through a focussing lens 39 which reduces the diameter of the infrared light beam in the direction of the sample to define the previously described minute region 13 of the sample into which the infrared light pulses 17 are directed.

The modulator 18 which cyclically interrupts the continuous infrared light beam 14 to generate the previously described sequences of discrete pulses 17 is a beam chopper of the type having the rim of an opaque rotatable disc 41 situated between source 16 and lens 39 in the path of the beam 14. Notches 42 at the rim of the disc 41 intermittently transmit the infrared light beam 14 to lens 39 and sample 11 as the disc is rotated by a drive motor 43. Other types of beam chopper known to the art may also be employed.

A laser 44, which may be of the He-Ne type for example, directs the probe light beam 22 along the surface 21 of sample 11 through another lens 46 which focusses the probe light beam down to a diameter less than that of the infrared light pulses at the region of intersection of the probe light and infrared light beams. The focal point of lens 46 is adjacent the sample region 13 which is to be analyzed and thus the probe light beam 22 expands after passing region 13. The previously described deflections of the probe light beam 22 are detected by a position sensor 47 located to receive the probe light beam after it has traveled past the sample 11.

Position sensor 47 may be of the known quadrant form which produces electrical output pulses in response to displacement of a light beam from a predetermined position with the amplitudes of the output pulses being a function of the degree of light beam displacement.

To suppress spurious deflection signals or circuit noise that may occur from any of a variety of causes, the output of position sensor 47 is connected to one input 48 of a lock-in amplifier or synchronous detector 49. Lock-in amplifier 49 may be of the known form which transmits only pulses having a frequency similar to or close to that of a reference signal applied to another input 51 of the amplifier. To generate the reference signal, a light source 52 and photodiode 53 are situated at opposite sides of beam chopper disc 41 with the photodiode being electrically coupled to the reference signal input 51 of amplifier 49. Notches 42 of the disc 41 intermittantly transmit light from source 52 to photodiode 53 and thus the photodiode produces a reference signal which is synchronous with the frequency of chopping of infrared light beam 14 into pulses 17. Thus amplifier 49 suppresses output pulses from position sensor 47 other than pulses which result from infrared light pulses 17.

The speeds of grating drive motor 38 of the infrared light source 16 and beam chopper drive motor 43 are both controlled by a selectable D.C. voltage from a control signal source 54. The control signal source 54 may be a manually adjustable voltage source but is preferably of the programable form which may also be responsive to a computer generated signal to enable computer control of the system as will hereinafter be discussed in more detail.

A sequence of infrared light pulses 17 of constant duration but progressively varying wavelength is produced by actuating control signal source 54 to provide a constant voltage 56a to motors 38 and 43 for a period sufficient to cycle infrared source 16 through the desired range of output wavelengths. The level of the control voltage 56a determines the duration of the infrared light pulses 17 as the speed of chopper motor 43, like that of the grating drive motor 38, is controlled by such voltage.

At the completion of a sequence of infrared pulses 17, the control voltage may be dropped to a lower level 56b to initiate another sequence of infrared light pulses having a longer pulse duration in order to analyze composition at a greater depth in the sample 11 as hereinbefore described. Grating drive motor 38 and chopper drive motor 43 then operate more slowly. The second, lower level 56b of control voltage is maintained proportionately longer in order to complete the second cycle. A capacitor 57 or other differentiating circuit is coupled between control signal source 54 and the tunable infrared source 16 to transmit a reset pulse to the infrared source in response to the control voltage change between sequences.

Additional sequences of infrared pulses 17 of longer pulse durations may be initiated by providing further reduced control voltage levels 56c of proportionately increased durations.

Any or all of a variety of data processing and display devices may be used to correlate deflections of the probe beam 22 with the infrared pulse 17 wavelengths that initiate such deflections. In the present system these include a chart recorder 58, an oscilloscope 59 and a digital computer 61 controlling a printer 62.

The output pulses from amplifier 49 control a first pen drive 63 that operates a first pen 64 of the chart recorder 58. The paper drive motor 66 of the chart recorder is controlled by the voltage from control signal source 54 and thus operates at a speed proportional to the momentary level of the control voltage 56a, 56b or 56c. Consequently, the paper 67 in the recorder 58 travels a constant distance during any given sequence of infrared pulses 17 as paper drive motor 66 slows in proportion to the slowing of infrared source grating drive motor 38 during successive sequences of increasing duration.

Thus during any given sequence of infrared light pulses 17, first pen 64 generates a graphical trace 68 on paper 67. Successive points along the base of the trace 68 correspond to the successive wavelengths emitted by infrared source 16 during the sequence of infrared pulses 17 and the paper 67 may be calibrated to indicate such wavelengths. The trace 68 exhibits peaks 69 at points which correspond to wavelengths at which strong infrared absorption occurred during the sequence. As previously described, the locations and relative sizes of such absorption peaks 69 along the trace 68 are distinctively different for each of the different constituents of coal. Thus the composition of the minute region 13 of the sample 11 may readily be identified, following direction of a sequence of infrared pulses 17 into that region, by identifying the peak absorption wavelengths that are present in the resulting trace 68 with the characteristic peak absorption wavelengths of specific coal constituents.

To indicate the depth in the sample 11 that is being analyzed by a particular trace 68, a second pen driver 71 for a second pen 72 may be controlled by the output voltage of control signal source 54. Thus in conjunction with the above described operation the chart recorder 58 also generates a second trace 73 having a level on paper 67 determined by the level 56a, 56b or 56c of the control voltage during the sequence of infrared light pulses 17. Paper 67 may be calibrated to enable reading of the depth of sample analysis from the location of the second trace 73.

A trace 68' similar to trace 68 as produced by the chart recorder 58 may also be generated, and be used for a similar purpose, by coupling amplifier 49 and control signal generator 54 to the vertical 74 and horizontal 76 sweep controls of oscilloscope 59. If the oscilloscope 59 is of the dual beam type, the output voltage from control signal source 54 may also be used to generate a depth indicating trace 73' similar to the trace 73 produced by the chart recorder 58.

Following analysis of one specific minute region 13 of the coal sample 11 in the above described manner, X-stepping motor 33 is actuated to bring an adjacent sample region of the sample into position to receive the infrared light pulses 17 and the sequence of operations is repeated to identify the composition of that region. After the regions 13 along an initial scan line have been analyzed, Y-stepping motor 29 may be actuated to enable similar operations along an adjacent parallel scan line and the process may be repeated to complete a microanalysis of any desired area of the sample 11. Z-stepping motor 36 may be used to position the sample relative to probe light beam 22 and to adjust for unevenness in the surface 21 of the sample, if necessary.

While the several components of the system may be manually actuated and controlled, it is also possible to use a computer 61 to cycle the control signal source 54, stepping motors 29, 33 and 36 and other components of the system. A switch 77 may be closed to transmit the control voltages 56a, 56b and 56c of control signal source 54 and output pulses from amplifier 49 to the computer 61 through an analog to digital converter 78 if the computer is of the digital form. The computer may then generate and transmit processed control signals to the above described components of the system through a digital to analog converter 78 if needed. Computer 61 may also operate a printer 62 which prints out, in graphical or digital form, data corresponding to that present in the traces 68 and 73 produced by chart recorder 58 together which coordinates identifying the location of the region 13 to which each such set of data relates. It is also possible, if desired, to automate the process fully by programing computer 61 to perform the hereinbefore described identification of the constituents of successive sample regions 13 by comparison of detected peak infrared absorption wavelengths with characteristic peak infrared absorption wavelengths of different specific coal constituents.

The foregoing description of a preferred embodiment of the invention has been presented for purposes of illustration and description. It is not intended to be exhaustive or to limit the invention to the precise form disclosed, and obviously many modifications and variations are possible in the light of the above teaching. The described embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. In a method of identifying chemical constituents of a localized region of a coal sample, the steps comprising:
   directing at least one sequence of infrared light pulses into said sample region from a location spaced apart from a surface of said coal sample,
   varying the wavelength composition of successive ones of said infrared light pulses of said sequence,
   detecting thermally induced index of refraction changes in the medium which is between said location and said surface of said coal sample that accompany optical absorption of said infrared pulses in said sample region, said index of refraction changes being detected by directing a probe beam of light along said surface of said coal sample and through the portion of said medium that is adjacent said sample region, and by detecting the amount of deflection of said probe beam at said portion of said medium that is caused by each of said infrared light pulses of said sequences thereof,
   correlating said index of refraction changes with the particular infrared light pulse wavelengths that initiate the changes, and
   identifying said chemical constituents by correlating said particular wavelengths with the characteristic peak infrared absorption wavelengths of specific coal constituents.

2. The method of claim 1 wherein said step of correlating said index of refraction changes with the particular infrared light pulse wavelengths that initiate the changes is accomplished by generating a graph wherein index of refraction change peaks are depicted as a function of the varying wavelength composition of successive ones of said infrared light pulses of said sequence whereby said characteristic peak infrared absorption wavelengths of specific coal constitutents may be readily identified.

3. The method of claim 1 wherein said sequence of infrared light pulses is generated by:
 directing a continuous beam of infrared light towards said sample,
 progressively shifting the wavelength composition of said continuous beam through at least a predetermined portion of the infrared spectrum, and
 cyclically interrupting said continuous beam to convert said continuous beam into discrete spaced apart pulses which have equal durations.

4. The method of claim 3 wherein the wavelength composition of said continuous beam of infrared light is progressively varied between a wavelength of about 3 microns and a wavelength of about 15 microns.

5. The method of claim 1 wherein said steps are repeated at said region of said sample utilizing an additional sequence of said infrared light pulses which are of different duration than the pulses of the first sequence thereof whereby constituents of said sample at different depths therein may be identified.

6. The method of claim 1 wherein said steps are repeated at each of a series of successive regions situated along a scan path on said sample whereby variations of the chemical composition of said sample along said scan path may be identified.

7. The method of claim 1 including the further steps of:
 directing a plurality of said sequences of infrared light pulses into each of a plurality of different regions of said sample,
 varying the pulse duration between successive ones of said sequences at each of said regions while maintaining the pulse duration substantially constant during each individual sequence, and
 repeating, in conjunction with each infrared light pulse of each of said sequences thereof, said steps of detecting thermally induced index of refraction changes, correlating said index of refraction changes with infrared light pulse wavelengths, and identifying constituents by correlating the wavelengths with peak infrared absorption wavelengths of specific coal constituents.

8. A method of analyzing the chemical composition of a coal sample comprising the steps of:
 transmitting a substantially monochromatic beam of infrared light towards a predetermined surface region of said sample from a location which is spaced apart from said sample,
 modulating said beam into a first sequence of separate infrared light pulses of substantially uniform durations,
 sweeping the wavelength of said beam from a first region to a second region of the infrared spectrum as said beam is being modulated into said sequence of separate light pulses,
 directing probe light along the surface of said sample in the vicinity of said predetermined region thereof,
 sensing deflections of said probe light which result from index of refraction changes in the medium which is between said location and said predetermined surface region of said sample that are induced by absorption of said infrared light pulses in said predetermined region of said sample,
 matching individual ones of said deflections with the particular infrared light pulse wavelength which causes the deflection, and
 identifying specific chemical components of said predetermined region of said sample by correlating said particular infrared light pulse wavelengths with characteristic infrared absorption wavelengths of different chemical components of coal.

9. The method of claim 8 including the further step of modulating said beam into a second sequence of separate pulses having a different substantially uniform duration to identify said chemical composition at a different depth in said sample.

10. The method of claim 8 including the further steps of successively transmitting said beam of infrared light towards each of a series of predetermined regions of said coal sample, modulating said beam into a sequence of separate infrared light pulses of substantially uniform durations while said beam is being transmitted to each of said regions, and sweeping the wavelength of said beam from a first region to a second region of the infrared spectrum during each of said sequences of light pulses to identify variations of said chemical composition of said sample at different portions thereof.

* * * * *